United States Patent
Zaromb

(12) 
(10) Patent No.: US 6,565,811 B1
(45) Date of Patent: *May 20, 2003

(54) APPARATUS FOR THE DETECTION OF HARMFUL SUBSTANCES OR TRACES THEREOF

(76) Inventor: Solomon Zaromb, 9 S. 706 William Dr., Hinsdale, IL (US) 60521

(*) Notice: Subject to any disclaimer, the term of this patent is extended or adjusted under 35 U.S.C. 154(b) by 170 days.

This patent is subject to a terminal disclaimer.

(21) Appl. No.: 09/613,246

(22) Filed: Jul. 10, 2000

Related U.S. Application Data

(63) Continuation-in-part of application No. 08/851,428, filed on May 5, 1997, now Pat. No. 6,087,183, which is a continuation-in-part of application No. 08/377,966, filed on Jan. 25, 1995, which is a continuation-in-part of application No. 08/255,712, filed on Jun. 7, 1994, now abandoned, which is a continuation of application No. 07/931,572, filed on Aug. 10, 1992, now abandoned, which is a continuation-in-part of application No. 07/993,080, filed on Dec. 18, 1992, now Pat. No. 5,328,851, which is a division of application No. 07/499,602, filed on Mar. 26, 1990, now Pat. No. 5,173,264, which is a continuation-in-part of application No. 07/330,654, filed on Mar. 30, 1989, now Pat. No. 4,912,051, which is a continuation-in-part of application No. 07/330,655, filed on Mar. 30, 1989, now Pat. No. 4,977,095.

(51) Int. Cl.[7] .................................................. G01N 1/18
(52) U.S. Cl. .............................. 422/88; 422/69; 436/52; 436/178; 55/423
(58) Field of Search ........................... 422/52, 56, 86, 422/88, 91, 89, 98, 69; 436/52–55, 165–167, 168, 172, 909, 161, 169; 55/161, 158, 167, 423

(56) References Cited

U.S. PATENT DOCUMENTS

| | | | | |
|---|---|---|---|---|
| 4,912,051 A | * | 3/1990 | Zaromb | 422/52 |
| 4,977,095 A | * | 12/1990 | Zaromb | 422/56 |
| 5,173,264 A | * | 12/1992 | Zaromb | 422/88 |
| 6,087,183 A | * | 7/2000 | Zaromb | 422/52 |

* cited by examiner

*Primary Examiner*—Lyle A. Alexander
(74) *Attorney, Agent, or Firm*—Solomon Zaromb

(57) ABSTRACT

The presence of carcinogens in air, soils, and other areas is detected by combining liquid-assisted air sampling with means for testing liquid samples for mutagenicity. Hazardous or illicit substances or pathogens which may be buried in the ground or otherwise concealed or present in contaminated food at various stages of food processing are detected using a two-line probe such that one of the lines directs exhaust air from the sampler onto suspect surfaces so as to dislodge and blow off droplets, particles or insects therefrom while the other line draws some of them into the sampler. Variants of said two-line probe can also serve to collect lead, hexavalent chromium or other harmful substances and bacterial, fungal or viral pathogens from crumbling walls or floors. Liquid-assisted air sampling can also serve to capture disease-transmitting insects and detect and identify insect-borne pathogens.

10 Claims, 5 Drawing Sheets

APPARATUS FOR THE DETECTION OF HARMFUL SUBSTANCES OR TRACES THEREOF

REFERENCE TO RELATED APPLICATIONS

Figure 1:
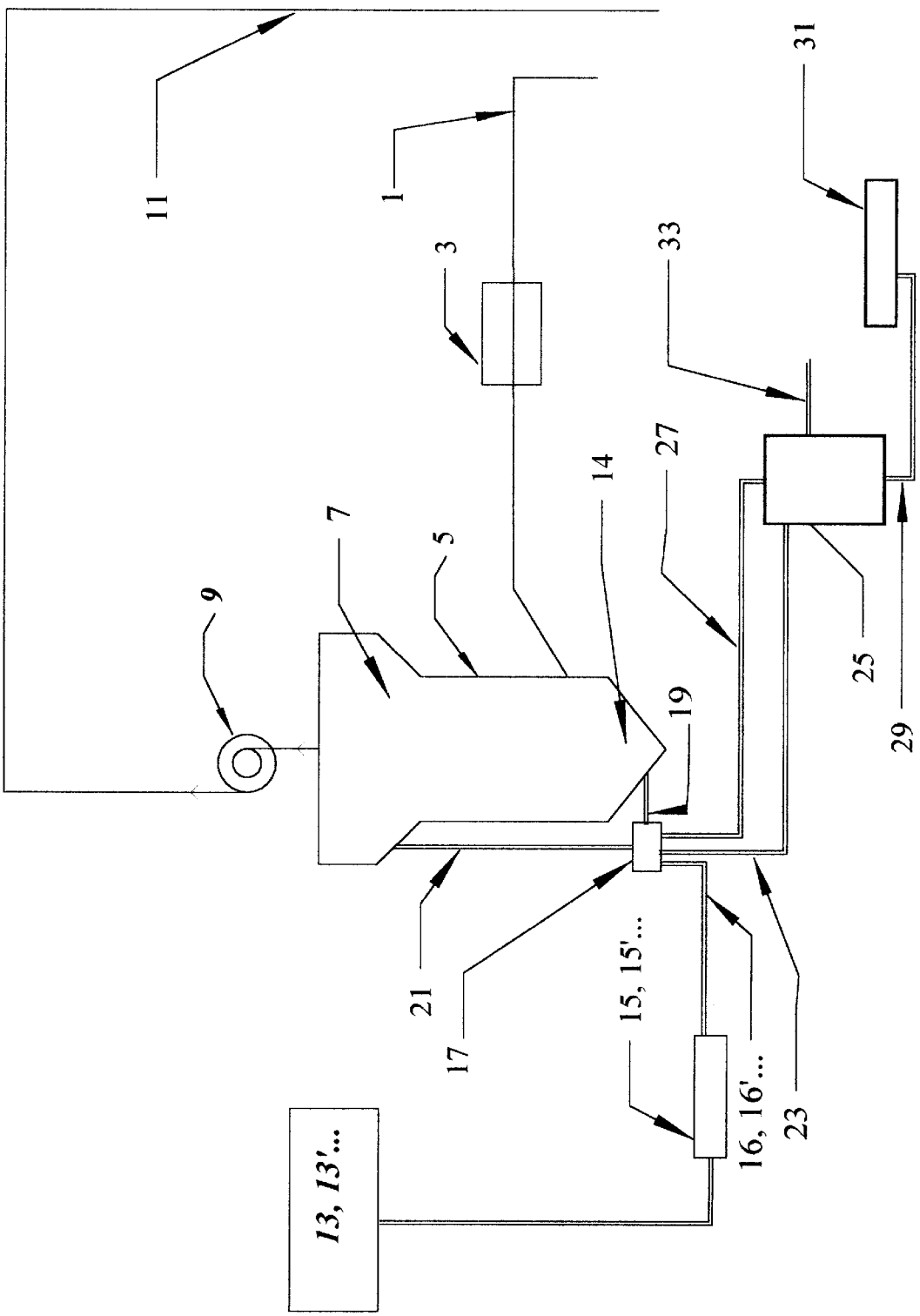

This is a continuation in part of application Ser. No. 08/377,966, filed Jan. 25, 1995, and of application Ser. No. 08/851,428, filed May 5, 1997, now U.S. Pat. No. 6,087,183 which is a CIP of application Ser. No. 08/377,966 which is a continuation of application Ser. No. 07/931,572, filed Aug. 10, 1992, now abandoned, and a continuation-in-part of application Ser. No. 08/255,712, filed Jun. 7, 1994, now abandoned, which is a continuations-in-part of application Ser. No. 07/993,080, now U.S. Pat. No. 5,328,851 which is a divisional application of application Ser. No. 07/499,602, filed Mar. 26, 1990, now U.S. Pat. No. 5,173,264, which was a continuation-in-part of U.S. applications Ser. No. 07/330,654, filed Mar. 30, 1989, now U.S. Pat. No. 4,912,051, and Ser. No. 07/330,655, filed Mar. 30, 1989, now U.S. Pat. No. 4,977,095.

The disclosures of all of said applications and patents are incorporated herein by reference.

BACKGROUND OF THE INVENTION

This invention relates to improved apparatus and methods for detecting harmful substances, whether airborne or grounded, whether biological or chemical, which may pose an immediate or long term hazard to human life or health.

In my afore-cited co-pending applications, I have disclosed apparatus and methods for collecting various contaminants—including vapors and particles, chemical or biological—from a large volume of air into a small volume of carrier liquid, so as to permit or facilitate rapid and ultra-sensitive detection of traces of hazardous or illicit substances which may be otherwise difficult to detect. The collected contaminants may be either dissolved by or suspended in the carrier liquid.

My earliest apparatus was intended mainly for the absorption of vapors by the carrier liquid and was therefore referred to as liquid-absorption air sampler. With subsequent use of the same apparatus for the collection of respirable particles, the term "absorption" became inappropriate, as the collected particles remain suspended in the carrier liquid without being dissolved therein. Such apparatus and methods will therefore be referred to herein as "HTLAAS" for High-Throughput Liquid-Assisted Air Sampling, which applies to collected air contaminants which are either dissolved or suspended in a carrier liquid.

The present disclosures deal with several improvements and new potential applications of said apparatus and methods which extend the applicability of the HTLAAS technology to new uses and to previously unmanageable or borderline atmospheric conditions. Some of the new uses include collection of pathogen-bearing insects. For the sake of brevity, collected insects will also be referred to as "particulates," especially after being killed or incapacitated in a HTLAAS device.

The applicability of HTLAAS devices can be extended to various types of hazards which have been heretofore dealt with by other means in much less cost-effective ways. For instance, the present approach of the Environmental Protection Administration [EPA] is to monitor air, soils, and other areas for the presence of certain listed known or potential carcinogens, while possibly overlooking some unlisted ones. Therefore a single generalized method of monitoring for mutagenicity will not only be much more cost-effective than monitoring for a multiplicity of listed carcinogens but will also alert people to the presence of possible carcinogens which are not included in EPA's list. In a recent well-publicized case, an increased incidence of brain tumors among workers in an Amoco laboratory could not be connected to the use or presence of any known carcinogen using existing analytical methods. The use of a water-assisted air sampler in conjunction with any of the known methods of testing aqueous solutions for mutagenicity, as claimed in my afore-listed co-pending applications, may thus provide a far more cost-effective and more powerful carcinogen alert than what is being used at present.

It is therefore another object of this invention to provide a cost-effective method and instrumentation for monitoring ambient air, soils, and other areas for mutagenicity.

A good measure of the performance of HTLAAS devices is the concentration factor F, which is proportional to the ratio of the concentrations in the liquid carrier and in air of the monitored air contaminant, hereinafter referred to as "analyte." The concentration factor F is defined by the equation $$F = \epsilon S / v_L \quad [1],$$

where $\epsilon$ is the sampler's collection efficiency, S is its air sampling rate, and $v_L$ is the volume of liquid in which the analyte is collected.

Most of the previous work on concentrating airborne contaminants into a carrier liquid sought to maximize the collection efficiency and the air sampling rate within the limits imposed by size, weight, and power requirements. No serious attention was given to increasing the concentration factor F by minimizing $v_L$. Yet by gathering the collected contaminants into a ten-fold smaller liquid volume we can achieve a 10-fold increase in their concentration within the liquid and hence in the overall sensitivity of the system.

It is therefore an object of this invention to greatly enhance the detection sensitivity of systems using liquid-assisted collection of airborne contaminants by minimizing the volume of the liquid into which said contaminants are gathered.

Present collection systems utilize primarily water-based carrier liquids, which have two important shortcomings, namely: [1] loss of water by evaporation during the sampling process; and [2] freeze-up of water at temperatures near or below 0 C. It is therefore also an object of this invention to overcome these shortcomings by substituting for the water an alternative carrier liquid having a much higher boiling point and lower freezing point.

Presently known water-assisted air-sampling systems have been used solely for detecting the presence of various of chemical or biological contaminants in ambient air. However, the same systems may also offer important advantages in the detection of concealed explosives, illicit drugs, or contaminated foods. It is therefore yet another object of my invention to provide an adapter that will permit collection by a liquid-assisted air sampling system of vapors or particles deriving from concealed hazards or illegal activities.

It is also an object of my invention to provide improved cost-effective apparatus and methods for capturing mosquitoes and other disease-transmitting insects in sufficient numbers to permit detection and identification of insect-borne pathogens.

Other objects of my invention are to provide an electronically programmable interface between a collector and a detector, so as to yield an automated or quasi-automated collection-detection system, to reduce the size and weight of the overall system, and to further enhance the system's sensitivity by further increasing its collection efficiency and air sampling rate.

More objects of the invention will become apparent to professionals in the chemical and biological defense, law enforcement, health monitoring, disease control, industrial safety and hygiene, environmental, chemical, metallurgical, and related areas following perusal of the complete specification.

SUMMARY OF THE INVENTION

Briefly, the invention consists of extending the applicability of liquid-assisted air samplers to several new uses and to operation of such samplers under extreme climatic conditions. The new uses are effectuated in the following ways:

1. Providing generalized means and methods of detecting the presence of carcinogens in air, soils, and other areas by combining liquid-assisted air sampling with means for testing liquid samples for mutagenicity.

2. Providing means and methods of detecting the presence of hazardous or illicit substances or pathogens which may be buried in the ground or otherwise concealed or present in contaminated food at various stages of food processing, said means comprising a two-line probe such that one of the lines directs exhaust air from the sampler onto suspect surfaces so as to dislodge and blow off droplets, particles or insects therefrom while the other line draws some of them into the sampler. Variants of said two-line probe can also serve to collect lead, hexavalent chromium or other harmful substances and bacterial, fungal or viral pathogens from crumbling walls or floors.

3. Providing means and methods of capturing disease-transmitting insects and detecting and identifying insect-borne pathogens.

4. Extending the sampler's operational range to extreme climatic conditions by substituting an organic low-vapor-pressure low-freezing-point carrier liquid, such as mineral oil, corn oil, or dimethyl sulfoxide, for the water in present liquid-assisted air samplers.

5. Extending the range of detectability of sampler-detector systems to lower air concentrations and smaller particle sizes by minimizing $v_L$ and increasing S and $\epsilon$ of Equation 1. The minimization of $v_L$ is achieved by transferring the collected analyte from an organic carrier liquid into a tiny volume of water, taking advantage of the differences in the densities of these liquids. The increases in S and $\epsilon$ are achieved by further improvements in sampler design.

6. The afore-said minimization of $v_L$ is preferably accomplished as part of an electronically programmable collector-detector interface which is geared for automated or quasi-automated air monitoring.

BRIEF DESCRIPTION OF THE DRAWINGS

The invention is best explained with reference to the drawings, in which:

FIG. 1 is a block diagram of the air and liquids flow system in several preferred embodiments of my invention;

FIG. 2 is a cross-sectional view of one variant of the device 5 of FIG. 1 together with a novel attachment thereto;

FIG. 3 shows two sectional views of one of several sampling tubules in another variant of device 5;

FIG. 4 is a cross-sectional view of an improved expansion chamber 7 in the device 5 of FIG. 1; and FIG. 5 is a schematic diagram of a novel concentrating device in another preferred embodiment of my invention.

DESCRIPTION OF THE PREFERRED EMBODIMENTS

The block diagram of FIG. 1 outlines the air and liquids flows in several preferred embodiments of my invention. Starting at the air intake line 1, the sampled air is drawn through an electrically programmable intake control valve 3 into a HTLAAS device 5, such as is described in my co-pending application Ser. No. 08/851,428, filed May 5, 1997, or in conjunction with my below-discussed FIGS. 2 and 3. After being partly scrubbed of its contaminants, the air is exhausted through a flow expansion chamber 7 by an air blower 9 into an air exhaust line 11. The design of expansion chamber 7 is shown in the below-explained FIG. 4.

The liquids flow circuits include the HTLAAS 5, the concentrator 25, liquid reservoirs 13, 13' . . . , and micro-pumps 15, 15' . . . for feeding metered doses of mineral oil and aqueous medium to the HTLAAS and concentrator, respectively, a programmable valving control comprising a multi-channel solenoid valve 17, and interconnecting lines 16, 16' . . . , 21, 23, 27, and 29, which are shown in the left and lower portions of FIG. 1 as double lines to distinguish them from the air flow circuit [drawn as single lines]. The electrically programmable valving control or multi-channel solenoid valving system 17 is used to close or open any of the lines 16, 16' . . . , 19, 21, 23, and 27 of FIG. 1 at predetermined intervals.

The liquids flow system comprises liquid reservoirs 13, 13' . . . , electronically controllable micro-pumps 15, 15' . . . , a programmable multi-channel solenoid valve 17, and connecting lines 16, 16' . . . , 19, 21, 23, 27, and 29. One or more liquid reservoirs 13, 13' . . . supply one or more liquids to a conical cavity 14 of the HTLAAS device 5 via micro-pumps 15, 15' . . . , liquid supply lines 16, 16' . . . , electrically programmable valving 17, and a liquid feed line 19. The liquid that is contained in the conical cavity 14, which serves as a liquid input chamber, is impacted by part of the air stream that is drawn in through the intake line 1, whereby droplets are formed and carried over so as to deposit as a swirling liquid film on the inner wall of a sampling tube 105 [FIG. 2], as described in my afore-cited co-pending application Ser. No. 08/851,428. At high air flow rates, some of that liquid is carried over and accumulates in the expansion chamber 7, whence it is either recirculated into the conical cavity 14 via line 21, valving 17, and feed line 19 or is diverted by valving 17 and line 23 into a concentrator 25.

Also fed into concentrator 25 is a scavenging liquid from one of the reservoirs 13, 13' . . . , micro-pumps 15, 15' . . . , and supply lines 16, 16' . . . through valving 17 and a scavenger supply line 27. The resulting contaminant-enriched scavenging liquid is fed from concentrator 25 to a detector 31 via a concentrated sample line 29, while the excess of depleted liquid is discarded via a waste line 33.

At appropriately programmed times, one or more liquid reservoirs supply a selected liquid to the HTLAAS via its associated micro-pump, the solenoid valve 17, and line 19; another reservoir supplies a scavenging solution 76 [FIG. 5] to a concentrator 25 via its micro-pump and line 27; and contaminant-enriched liquid carrier is fed by gravity from the expansion chamber 7 through line 21, valve 17, and line 23 into the concentrator 25 at time intervals and for durations controlled by the programmed solenoid valve. The liquids flow system of FIG. 1 permits automated feeding of particulate-enriched liquid samples to detector 31, which may comprise any appropriate sensor or array of sensors.

The device 5 of FIG. 1 may be any suitable high-throughput sampler in which a substantial part of contaminants from the sampled air is retained within a liquid solution or suspension. The portable HTLAAS of my co-pending application Ser. No. 08/851,428 and the apparatuses disclosed in my other above-referenced applications and patents are included in this category. Also included are modified versions of these devices, such as those indicated in FIGS. 2 and 3.

Figure 2:
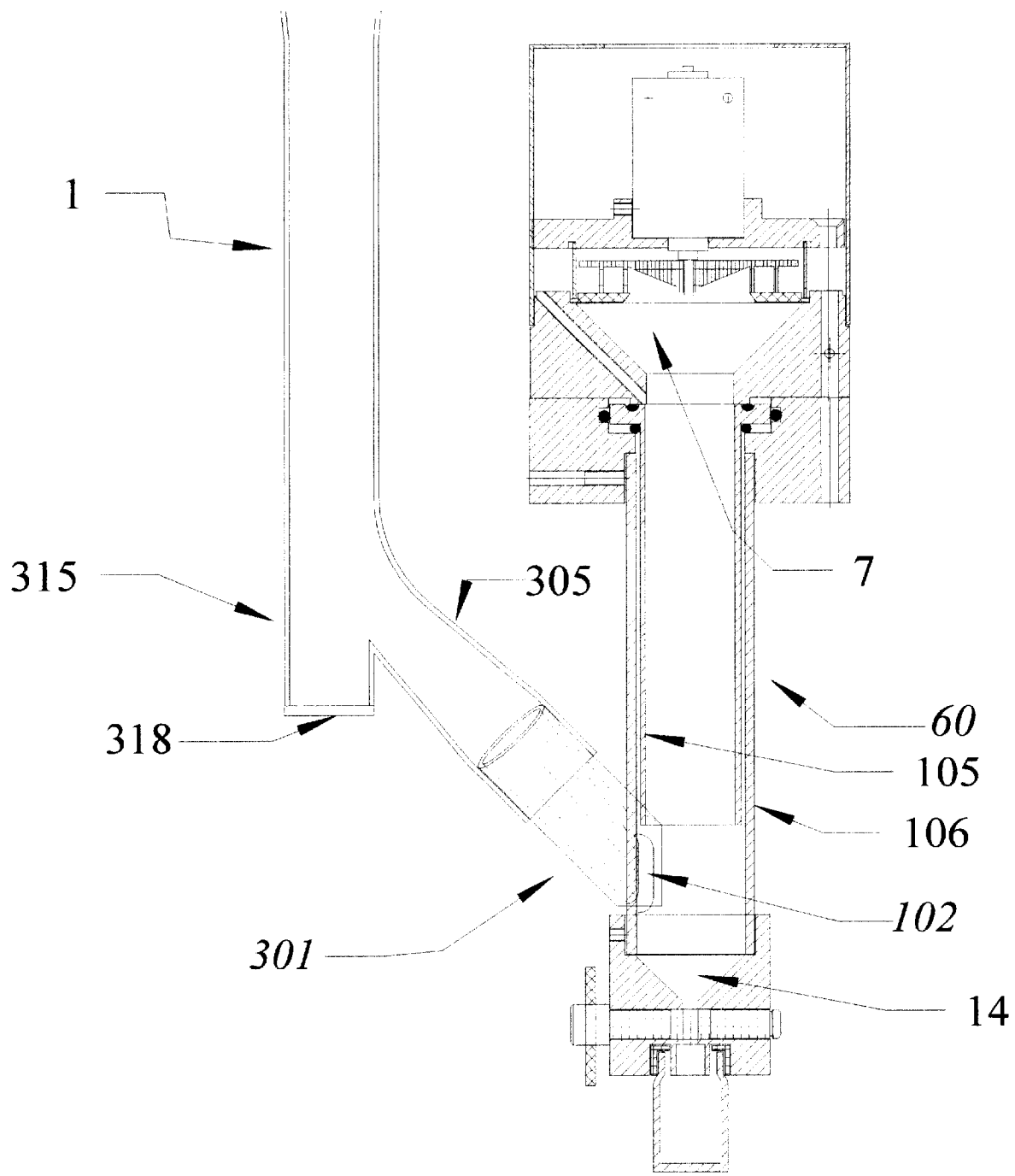
Figure 5:
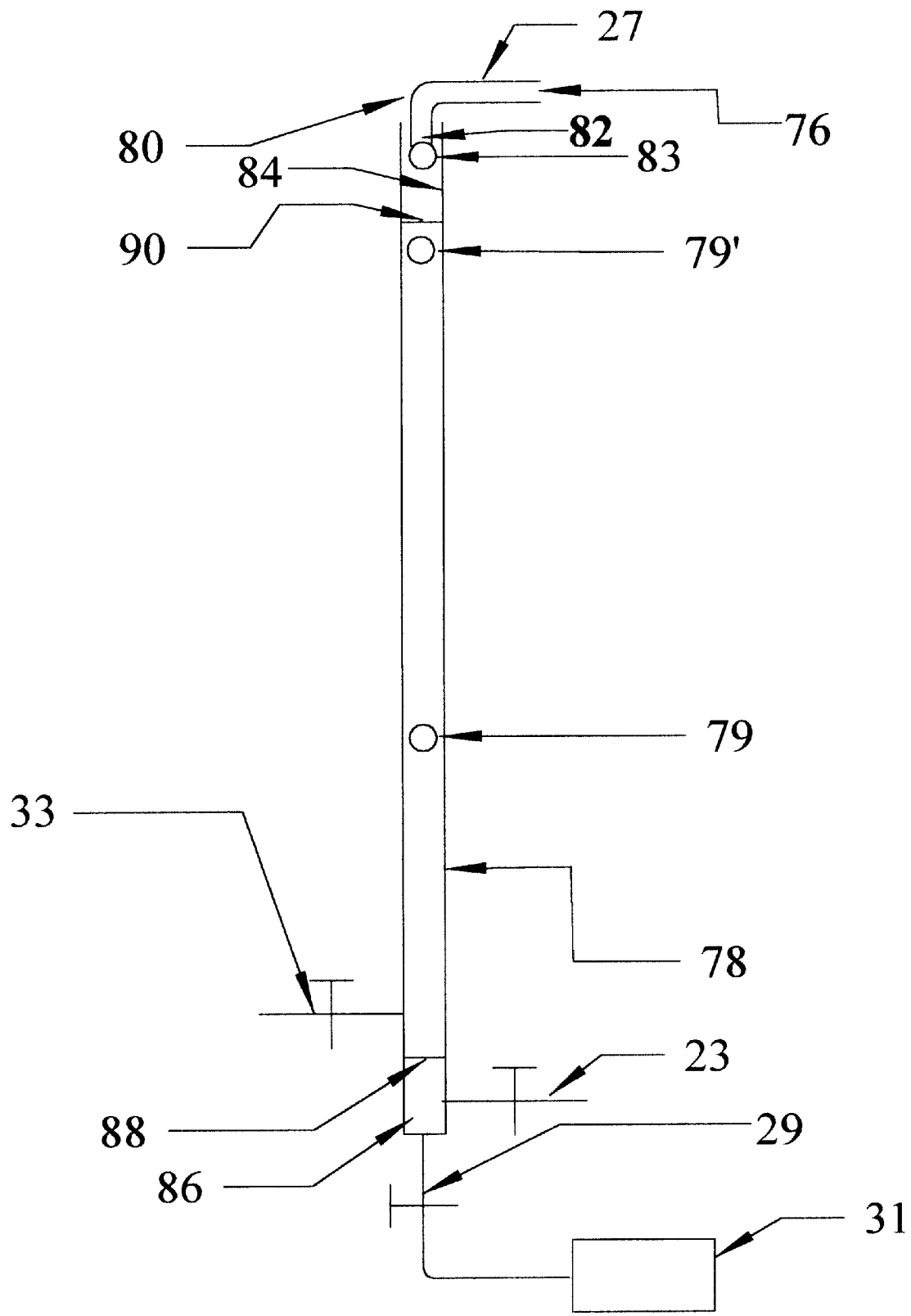

FIG. 2 shows a Portable HTLAAS or PHTLAAS 60, such as that shown in FIG. 5 of my co-pending application Ser. No. 08/851,428 and described in detail therein. An adapter 301 to the air inlet 102, similar to that shown in FIG. 17 of said co-pending application, is connected to the air intake line 1 by a smoothly curved arm 305 of an inverted Y-junction. A second, straight, arm of the Y-junction serves as a large particles trap 315, ending with a capped opening 318 which provides access for removal of the trapped large particles at appropriate time intervals. As air is drawn through arm 305, the suspended smaller particles follow the curved streamlines, whereas the inertia of the larger particles causes them to continue along a straight path into trap 315. Any accumulation of large particles can be removed from trap 315 by uncapping the opening 318. Such a Y-junction serves to intercept interfering large particles [>10 microns in size] in cases where only respirable [<10-micron-size] particles are to be monitored.

As shown in FIG. 2, the PHTLAAS 60 comprises an outer protective tube 106 and an inner sampling tube 105 leading to the expansion chamber 7. However, to improve the collection efficiency for smaller particles [1–2 microns or less in size], without significantly increasing the required power consumption, it may be advantageous to replace the single tube 105 by several smaller sampling tubules, such as that shown in FIG. 3.

The rationale for replacing the single sampling tube of the PHTLAAS by a plurality of smaller tubules is that the minimum particle size that can be collected by a cyclone or similar air sampler is proportional to the square root of its diameter [see, e.g., J. H. Maas, "Gas-Solid Separations," in *Handbook of Separation Techniques for Chemical Engineers*, P. A. Schweitzer, editor-in-chief, Section 6.1, pp. 6-3 through 6-17, McGraw-Hill, New York, 1979]. This implies that a four-fold reduction in sampling tube diameter should raise the collection efficiency for 1-micron particles to the value that is obtainable with 2-micron particles and the larger diameter.

It also follows from the equations governing the design and performance of cyclone collectors that multiple tubules of smaller diameter yield higher collection efficiencies than a single large tube under otherwise comparable conditions, even if the tubules are of shorter length than the large tube. With shorter tubules, the required power decreases for otherwise comparable flows.

Figure 3:
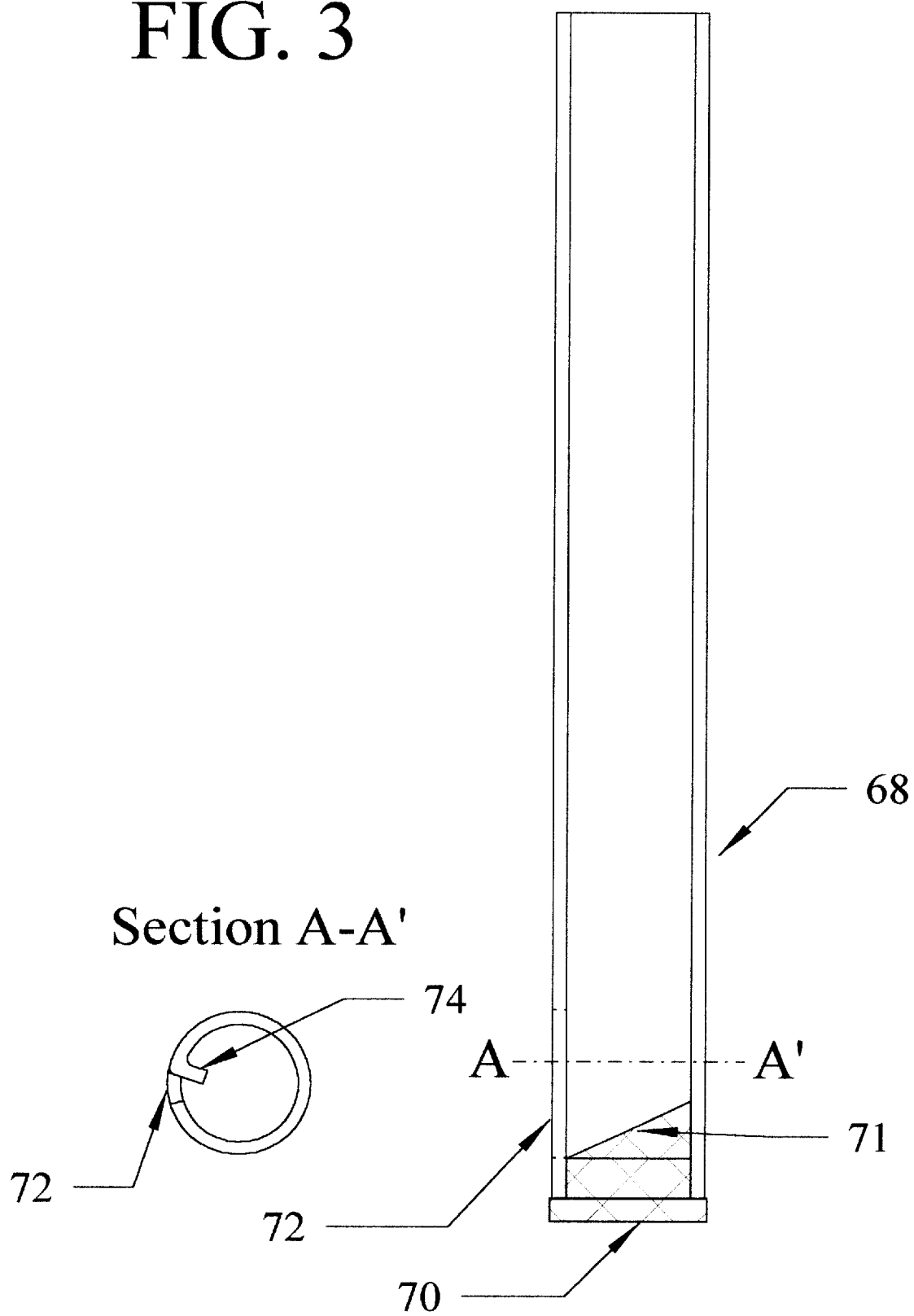

For instance, in the PHTLAAS of FIG. 2, the single 1.1" sampling tube 105 was replaced by three parallel 0.53"-I.D. sampling tubules, such as tubule 68 of FIG. 3. To induce a swirling air flow within the tubules, each of them is capped off at its lower end with a polyethylene plug 70 having the form of a short cylinder with its upper end 71 cut at an angle of 30° to its axis, as shown in FIG. 3. The lower end of that cut faces a ⅝"-high ³⁄₁₆"-wide slot 72, so that any draining liquid can flow down the 30° slope and out through the slot. Tubule 68 is made preferably of a thin thermoplastic material, such that it permits forming a louver 74 by making one vertical and two parallel horizontal cuts in the tubule so as to form three edges of a rectangle and pushing in the rectangular area so as to swivel it inward around the second vertical edge of the triangle, thus forming the structure shown in Section A–A' of FIG. 3. This design imparts a swirling motion to the air flow within the tubule and assures that there are no obstructions that might cause clogging or retention of collected particles.

Operation at maximal sampling rates is desirable for two reasons. First, the amount of any collected air contaminants is proportional to the sampled volume and hence to the sampling rate. Secondly, the minimum particle size that can be collected by a cyclone or a related device is inversely proportional to the square root of the sampling rate. Therefore, to increase the collection efficiency for 1-micron particles, the sampling rate should be as high as practicable for a given sampler. The main factor which limited the sampling rate in the older PHTLAAS versions was excessive entrainment of liquid droplets by the outflowing air. This limitation was largely overcome by the modified fan-impeller configuration of FIG. 4, in which the outflowing airstream must go around a co-rotating baffle before reaching the exhaust fan. As the baffle co-rotates with the impeller, the larger droplets impinging upon it are spun off centrifugally onto the wall of the expansion chamber, whence they are collected into a liquid-retaining channel. Also spun off are particles which impinge on the co-rotating outer rim under the base of the impeller. It is thus possible to increase the sampling rate to 400 l/min, still without significant entrainment, with a rather low power input.

Another effect that was noticed at the higher flow rates was a gradual accumulation of liquid in the upper expansion chamber and depletion of liquid in the lower conical cavity. To prevent such accumulation and depletion, the expansion chamber was modified to yield the liquid re-circulation and collection system of FIGS. 1 and 4, which also provides a programmable interface to a sensor or a sensor array.

Figure 4:
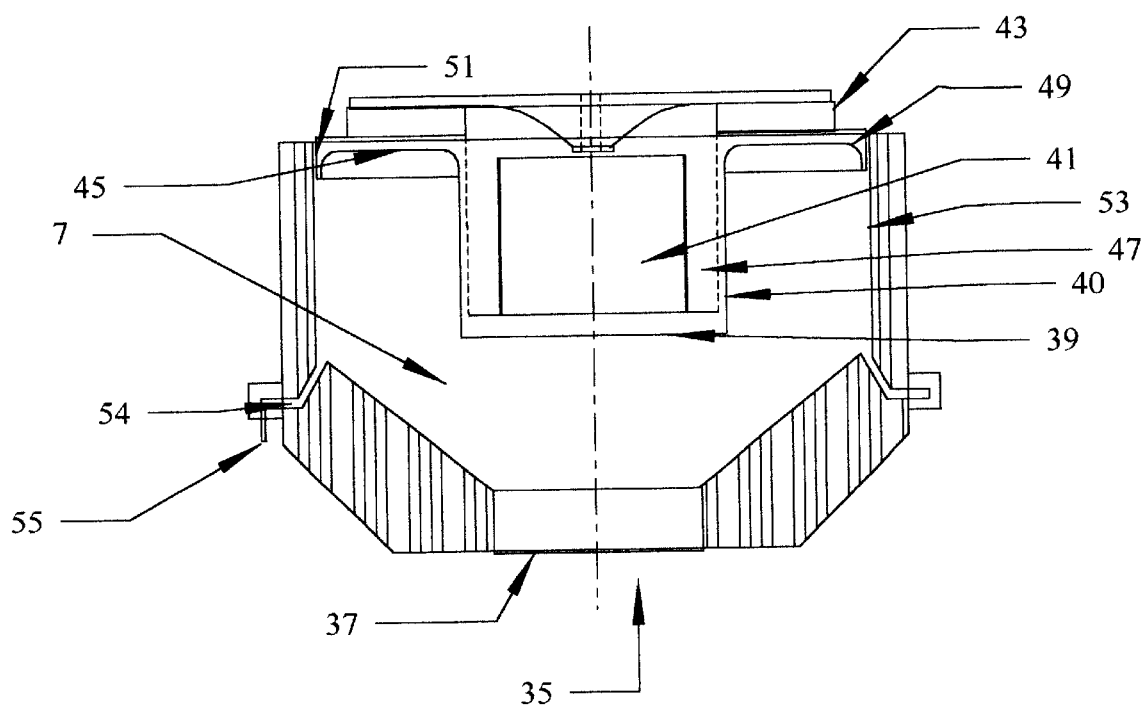

That system keeps removing liquid through line 21 from the retaining channel 54 of FIG. 4 by gravity whenever line 21 is filled with liquid. The setting of the electrically programmable solenoid valve 17 determines then whether the draining liquid is to feed a detector (or array of detectors) through lines 23 and 29 or simply be re-circulated into the conical cavity through line 19.

To keep line 21 filled [i.e., bubble-free], liquid is continually fed from one of the reservoirs 13, 13' by one of the electronically controlled micro-pumps 15, 15' and forced upward from the bottom of line 21 so as to expel any trapped bubbles. The micro-pump is adjusted to supply the liquid at a rate that is sufficient to compensate for depletion by evaporation, entrainment, and sample withdrawals to the detector.

As shown in FIG. 4, the expansion chamber 7 is designed to minimize entrainment of droplets and particles with the exhausted air stream and to permit recirculation and/or withdrawal of the contaminant-enriched liquid solution or suspension that is generated by the interaction of the sampled air stream with the liquid carrier. The air stream 35 leaving the sampling tube or tubes of the HTLAAS, such as one of those shown in FIG. 3, and entering chamber 7 through an opening 37, must go around or impinge upon a baffle 39 before being drawn through windows 41 into an exhaust fan impeller 43. Baffle 39 and windows 41 form part of an integral cap-shaped piece 40, made preferably of a plastic material such as polyethylene or polypropylene, which is affixed to the base of impeller 43, so as to co-rotate with it. Three wide substantially identical and symmetrically disposed windows 41 are cut out of the cylindrical wall of the inverted cap 40 so as to leave baffle 39 suspended on three equidistant legs 47 which form the vertical edges of windows 41. The rim 45 of cap 40 is affixed to impeller 43 on its flat upper side and has a rounded bevel 49 along the rim of its lower side which permits smooth transfer of impinging particles and water droplets towards the inner wall 53 of chamber 7 by the centrifugal action of the rotating rim. The outermost edge 51 of cap 40 and the inner wall 53 of chamber 7 form a fine clearance which is barely sufficient to permit free rotation of the cap but too small to permit outflow of any significant part of the air stream.

The particles and droplets which are cast off the rim 45 onto the chamber wall 53 flow down that wall into a liquid-retaining channel 54 and thence through a connecting tubule 55 into the recirculating line 21 of FIG. 1.

Another improvement is the replacement of aqueous media by a non-volatile liquid, such as light mineral oil as the carrier fluid in the PHTLAAS. If otherwise allowable, substitution of a non-volatile liquid for water greatly improves the performance of a PHTLAAS by preventing dry-ups or freeze-ups under some weather conditions and extends its applicability to a wider range of ambient temperatures, from as low as −30 C. to as high as 50 C. By cutting out evaporation losses, the use of mineral oil permits long-lasting operation over a wide temperature range without need to frequently replenish the liquid or precondition the temperature and humidity of the air stream.

For instance, following injection of about 10 ml of mineral oil, the liquid film within the sampling tube exhibited a swirling flow pattern over the entire inner surface, as pronounced as with water or perhaps even more so, which did not deteriorate after the sampler had been operated mostly unattended for over six hours at sampling rates of 200–300 l/min.

The apparatus for substituting an alternative liquid carrier, such as light mineral oil, corn oil, or dimethyl sulfoxide, for the water or aqueous solutions that are currently used in HTLAAS devices and for separating any captured biological agents or other suspended matter from the lighter oil by gravity with the aid of sinking water droplets, is indicated in FIG. 5. Nonporous solid particles are usually heavier than water, and even living microorganisms, whose density is close to that of a saline solution, i.e., ≧1.0 g/milliliter, would tend to settle out of the lighter oil [density≦0.83 g/milliliter] if not prevented by mixing [convection] and surface action or colloidal effects. If the suspension is confined within a vertical tubule 78 whose I.D. is not much larger than the diameter of sinking water droplets 79, 79', then the droplets will act as nets, scooping up and sweeping down the suspended matter along their way. This should accelerate the settling of suspended matter and of most hydrophilic solutes within a tiny water layer at the bottom of tubule 78 of FIG. 5.

A possible objection to the substitution of mineral oil or other non-aqueous liquid for the heretofore used water or aqueous as the liquid carrier in HTLAAS devices is that non-aqueous liquids are not compatible with most of the highly sensitive biological agent detectors, such as immunoassay-based sensors. Moreover, for maximum sensitivity, it is desirable that all or most of the captured particles be gathered into the smallest practicable volume of the final liquid sample that is fed to detector 31. The concentrating device of FIG. 5 solves the compatibility problem while minimizing the volume of the final liquid sample by efficiently transferring the captured particles from an oil carrier to a tiny volume of water.

According to FIG. 5, an aqueous medium 76 is fed through line 27 to a fine nozzle 80 whose orifice 82 faces downward, is coaxial with the inner wall 84 of tubule 78, and delivers droplets whose diameter is not much less than that of said inner wall. To prevent losses of droplets by accidental contacts with and wetting of that wall, tubule 78 is made of a hydrophobic material, such as Teflon or polyethylene. As the droplets 79, 79' sink down through tubule 78, they scoop up or sweep along any encountered suspended particles and finally form or merge with a lower aqueous layer 86. When the level 88 of that layer reaches the level of a valve-controlled line 33, the flow of droplets is interrupted, Line 33 is opened, and the oil is allowed to exit through it to an oil waste container. Once the oil has drained out of tubule 78, Line 33 is closed and valve-controlled Line 29 is opened, so as to allow the contaminants-enriched aqueous layer to drain into a detector 31. Once this drainage is completed, Line 29 is closed and tubule 78 can be refilled with a new contaminant-enriched oil suspension through the now opened Line 23 until the oil level 90 reaches a predetermined height range.

For the device of FIG. 5 to work best, the diameter $d_d$ of droplet must be carefully selected and matched with the internal diameter [I.D.] of tubule 78, $D_t$. For the droplet to sink easily, there must be enough room for the displaced oil to slip around it, which implies that the horizontal cross-sectional area of the droplet should not be larger than half of that of the oil column. This imposes the inequality:

$$d_d^2 \leq D_t^2/2 \qquad [3],$$

which also implies that a smoothly sinking droplet can not encounter and scoop up or sweep down more than 50% of the particles that are suspended in the column. Therefore, for each droplet to be most effective, the Inequality 3 should be close to an equality, i.e., $$d_d \approx D_t/\sqrt{2} \approx 0.71\, D_t \qquad [4].$$

Another important design consideration is the value of $d_d$. Since the volume is proportional to $d_d^3$, minimization of $d_d$ with adherence to Equation 4 should also minimize the final water volume. However, two important factors will prevent us from pushing such minimization too far. First, as droplet size decreases, surface effects become important and slow down the sinking rate. Second, as $d_d$ and $D_t$ decrease, the column height required to accommodate the 1- to 10-ml volume oil samples from a PHTLAAS may become unmanageable. For instance, a 25-cm long column would require a cross-sectional area of at least 0.04 cm² to accommodate 10 ml of oil. This would require $D_t$ to be at least 0.23 cm and $d_d$ to be about 0.16 cm [according to Eq 4], yielding a droplet volume of around 0.003 ml, which is one tenth of the 0.03-ml droplet volume that is usually coming out of a glass pipette. The smaller volumes can be generated by reducing the orifice size and substituting a less hydrophilic material for the glass. Thus, the basic approach reduces to optimizing $d_d$ within the range 0.16 cm≦$d_d$≦0.3 cm, while adhering to Equation 4, to implement the design of FIG. 5.

Therefore, to provide a collector-to-detector interface yielding a minimal sample volume, the components of FIG. 5 must satisfy the following requirements for an optimal design. First, to generate water droplets of various known sizes within a selected range, e.g., of 0.2–0.3 cm, the nozzle 80 must be made of such materials as glass, metals, Nylon, Teflon, polyethylene, polystyrene, etc. The droplet size generated by a nozzle made of each of these materials can be deduced from the number of droplets required to yield a fixed volume of water. The rate at which a droplet of each size sinks through a column of mineral oil or similar non-aqueous liquid can then be accurately timed. For instance, in one test, it took 24 seconds for a 0.05-ml droplet of red wine to sink through an 8-cm column of white mineral oil.

For example, the best values of $d_d$ and $D_t$ and of the column height H required to accommodate a 10-milliliter volume can be deduced from the formula $$\pi D_t^2 H/4 \approx 10 \text{ cm}^3 \qquad [5].$$

Should Eq 5 yield a length H that is unmanageably long, then one can resort to a more complex concentrator having n parallel columns of lesser height h, such that nh=H. The shorter columns also offer the advantage of shorter sinking times and hence faster separation of suspended particles from the oil.

The afore-disclosed apparatus can be used in various ways depending on the hazards which are to be monitored or detected, as illustrated by the following examples.

1. Detection of Concealed Explosives or Illicit Drugs

A successful system to detect explosives in buried mines and unexploded ordnance (UXO) must overcome the problem that the vapor concentrations of some of the buried explosives are so low as to preclude their reliable detection by even highly advanced vapor analyzers. For instance, cyclonite [RDX] and pentaerythritol tetranitrate [PETN] have equilibrium vapor pressures of the order of a trillionth of an atmosphere. Although the equilibrium vapor pressures of other explosives, such as trinitrotoluene [TNT], are about 1000 times higher than those of RDX or PETN, their actual vapor pressures near a buried mine will be lower than the equilibrium pressure by several orders of magnitude because of depletion of vapor molecules by adsorption onto the surrounding soil or dust particles and by being carried away by prevailing winds. The distribution profile of explosives molecules near a buried mine may therefore be expected to be mainly in the form of adsorbates onto soil particles exhibiting a concentration maximum at the depth of the mine and a minimum at the surface. Above the surface, any explosives molecules are likely to be present in the form of adsorbates onto dust particles or onto wind-blown soil particles rather than in vapor form. Moreover, the process of partial sublimation of a buried explosive and its adsorption onto the surrounding soil particles must be rather slow, especially with explosives of very low vapor pressure. Therefore, the actual concentrations of explosives adsorbates will be highly dependent on the length of time since the explosive was first buried. These concentrations may be expected to be substantially nil around a freshly buried mine and reach nearly constant plateaus after several months or years of burial. Therefore, to detect explosives that have been buried for relatively short lengths of time [hours, days, or a few weeks] an extremely high sensitivity is required. This can be achieved with a system comprising [a] means for transferring subsurface soil particles into [b] an appropriate collector and thence to [c] an appropriate sensor or sensor array for ultra-low-level detection and identification of any buried explosives.

Chemical detection of buried explosives is a particularly daunting technical problem. Because of their low vapor pressures and the limitations of detection technology, it is necessary to preconcentrate any captured traces of the analytes before introducing them into a detector. The above-discussed partial sublimation and adsorption of explosives molecules onto nearby soil particles may be viewed as a natural preconcentration process, which may be exploited for detection purposes by collecting some of these nearby particles and extracting adsorbates therefrom.

One way of collecting soil particles for such an analysis would be by mechanically scraping or digging into the surface and scooping up the loosened particles. However, such a mechanical action may cause enough disturbance to trigger an unwanted explosion. Gently swabbing the soil surface may be effective in cases where the surface particles contain a detectible concentration of explosives adsorbates. However, due to the expected steep concentration gradients emanating from a buried explosive, the probability of encountering detectible adsorbates will be vastly enhanced by probing deeper beneath the surface. A gentle, impact-free, and hence presumably safe method of such below-surface probing would consist of blowing particles off the soil and collecting some of the blown off particles into a high-volume air sampler, using exhaust line 11 in conjunction with intake line 1 of FIG. 1.

As already noted, the detection of airborne chemical explosives in trace concentrations presents a formidable challenge to existing sensing technologies primarily because of the extremely low concentrations of explosives that may be present in the vapor phase, especially in the case of the relatively non-volatile "plastic" explosives, such as RDX or PETN. In view of the extremely low vapor concentrations, it seems almost miraculous that dogs have been known to succeed where no present vapor analyzer could even contend. The dogs' successes, widely attributed to their ultra-sensitive olfactory system, may have been at least partly helped by the tendency of non-volatile vapors to preferentially adsorb onto particulates or be absorbed by water. Therefore, the surfaces of soil particles surrounding a buried mine may be partly covered by adsorbed explosives and, when these particles are blown into the air by a wind, they may carry with them a sufficient concentration of explosive material to be detected by a dog's highly sensitive nostrils following inhalation, retention, and dissolution in the nostrils' liquid lining. If this interpretation of the dogs' successes has any merit, then a system which captures particulates from a large volume of air and concentrates them into a small volume of liquid extractant which is fed to an appropriate detector would most effectively mimic the dogs' prowesses.

Such a system is represented by the block diagram of FIG. 1. For instance, what is lacking in the sensitivity of any man-made detectors as compared with that of the dog's nostrils may be at least partly made up by the much faster throughput of a PHTLAAS—about 300 liters/min, as compared with the dog's breathing rate of only a few liters/minute. Also, man-made instruments possibly approaching the sensitivity of a dog's nostrils may be fluorescence-labeled or radioactivity-labeled displacement immunosensors, such as that reported by U. Narang, P. R. Gauger, A. W. Kusterbeck and F. S. Ligler, "Multianalyte detection using capillary-based flow immunosensor," *Anal Biochem,* 255:13–19 (1998), which offer the advantages of high sensitivity and measurement speed for the detection of low-vapor-pressure explosives of special interest, such as TNT, RDX or PETN. A sensor of this type may be included in detector 31 of FIG. 1.

Immunosensors can also serve for high-sensitivity detection of drugs and various other substances, whether chemical or biological, including viruses and bacterial or fungal cells. Several low-vapor-pressure illicit drugs, such as cocaine or heroin, will similarly slowly adsorb onto surrounding dust particles, especially on dust settling near or on the packaged drugs, and such particles when blown off by exhaust line 11 may similarly reveal the presence of the drugs when picked up by intake line 1.

Moreover, whereas a dog's nostrils can only pick up particles which are blown by a wind off the soil surface, the PHTLAAS of FIG. 1 can pick up the more heavily explosives-covered particles from below the surface using an attachment, such that the air exhaust and air intake lines from and to the PHTLAAS terminate as two nearby parallel pipes, one of which serves to blow soil particles out from beneath the surface, while the other line serves to draw some of the blown off particles into the air sampler for extraction of adsorbates and immunosensing. An adjustable fixture [not shown] for holding the two pipes in a fixed relationship permits adjustments in the positioning and distance between the two pipes so that the amount of soil particles drawn in by the intake line is large enough to yield a hefty signal but not so large as to cause clogging problems.

As estimated below, either the intake line opening should be sufficiently far away from that of the exhaust line to keep the average concentration $c_s$ of the sampled airborne soil particles below about 0.007 g/L or else a programmed solenoid valve 3 may keep that opening blocked except for a short time interval during which only particles originating from the deepest levels will be picked up in an amount not exceeding about 2 g.

To adapt present PHTLAAS instruments for collection and desorption of soil particles and for feeding an analyte-enriched liquid extractant to an immunosensor, it is necessary to provide [a] the liquid flow system that is indicated on the left side of FIG. 1; and [b] a waste outlet for the processed particles, as indicated by line 33.

None of the previously disclosed work on the collection of airborne particles by PHTLAAS devices dealt with dust-laden atmospheres. The high particle concentrations generated by blowing the exhaust air into the soil may cause clogging problems unless proper precautions are taken. If the volume $v_e$ of extractant in the PHTLAAS is to stay at least 10 times larger than that of the soil particles, $v_\sigma$, then the total weight of particles [of average gravity $\rho_s \cong 2$ g/cc] that are subjected to extraction at any time must not exceed about 2 g for $v_e \cong 10$ ml. If the residence time $\tau_s$ of a soil particle within the PHTLAAS is about 1 min, then a steady state rate of uptake and removal of these particles must not exceed $v_\sigma \rho_s / \tau_s \cong 2$ g/min, which implies that for an air flow rate $V_A \cong 300$ L/min, the average concentration $c_s$ of airborne soil particles should not exceed $$c_s = v_\sigma \rho_s / \tau_s V_A \cong 0.007 \text{ g/L} \qquad [6].$$

Therefore, either the spacing between the air intake and air exhaust openings must be set far enough for the intake to pick up the less dense portions of the generated dust or a solenoid valve must cause the intake opening to be blocked most of the time, as suggested above.

To prevent an excessive build-up of particles within the PHTLAAS, the average rate of removal of processed soil particles should approximately equal the average rate of uptake, i.e., about 2 g/min or 1 cc/min under the above-postulated conditions. Such a rate of removal can be either continuous, with a permanently open drain, or intermittent, i.e. controlled by a large-bore solenoid valve [not shown].

The waste from the processed soil particles can be either disposed of in the field or stored in a container [not shown]. If the average rate of removal of processed particles is about 1 cc/min, then uninterrupted operation over an eight-hour shift would require a waste container size of at least 0.5 L, and preferably 1 L to accommodate >8 hours of operation. Similarly, the liquid flowing through the detector at a rate of about 0.1 ml/min will require a container of about 50–100 ml to dispose of the liquid waste over a similar length of time. The much larger volume of analyte-enriched extractant generated in the extraction process could be either discarded in the field or saved in properly marked vials for follow-up analyses.

The air flow of about 300 L/min through the intake and exhaust lines can yield a wide range of air velocities by adjusting the cross sectional area of the exhaust opening. For instance, an area of 1 cm$^2$ yields an average air velocity of about 50 m/s, which is more than adequate to blow a sizable hole in most soils. A hole at least 1" deep generated within about 1 minute would yield about 25 g of blown off soil for an average concentration of about 0.1 g/L of particles suspended in an air stream of about 300 L/min. The position of the intake opening should then be so adjusted that only about 10% of these particles get picked up by the PHTLAAS. Alternatively, the exhaust and intake openings may be adjacent to each other, but a two-way solenoid valve in the intake line could be timed so as to allow the dusty air to be drawn for only the last few seconds so as to pick up only the deeper soil particles.

To satisfy the requirements of rapid and efficient dissolution of explosives adsorbates from soil particles and of compatibility with satisfactory operation of the PHTLAAS and of the immunosensor, it may be necessary to introduce two separate liquid extractants—acetone followed by the immunosensor's buffer solution. Acetone is known to be a very efficient extractant for explosives in soil, but its high volatility would cause it to dry up rapidly in the hefty air stream of the PHTLAAS. However, by injecting an excess of acetone in the first minute of air sampling and following it up with an aqueous buffer solution while an adequate portion of the acetone still maintains full wetting of the particles, we can effectuate a transfer of dissolved adsorbates from the acetone into the buffer solution, which will be followed by complete evaporation of the acetone from the buffer before its withdrawal into the immunosensor.

The timing of the air flows through the PHTLAAS will have to be adjusted to conform with an optimal extraction treatment, preferably by an electrically programmable control means. For the entire sampling and extraction process to be effectuated rapidly, the air flow may be set at a maximum rate, so as to draw the desired amount of soil particles into the PHTLAAS in the shortest practicable time. The flow may then be reduced upon injection of the acetone to a rate that will suffice to keep the mixture stirred up and swirling but without causing too rapid an evaporation of the acetone. The flow may then be increased upon injection of the buffer solution to speed up the transfer of the analyte into the buffer and the evaporation of the remaining acetone. Finally, the air flow may be stopped to permit withdrawal of the analyte-enriched extractant and drainage of the treated soil particles. With each of these steps lasting a fraction of a minute, the entire cycle may be completed within 2–3 min.

2. Monitoring for Pathogens in Food Processing Plants

In another embodiment of my invention, an alternative potential use for the system of FIG. 1 is in the food processing industry. To monitor for harmful bacteria, molds, or viruses in processed foods, the exhaust line 11 should have an adjustable orifice [not shown] which is provided with a HEPA [High Efficiency Particulate Arrestance] filter that will remove contaminants from the exhaust air. The orifice should be adjusted for a sufficiently wide opening to yield only a moderate exhaust air velocity that will barely suffice to blow off some droplets from liquids or loosely lodged particles or insects from solid or semi-solid foods without causing any significant splashing from the monitored areas. Some of the blown off droplets, particles or insects can then be drawn into a HTLAAS device 5 by the intake line 1 and collected in a film of mineral oil along the surfaces of the sampling tube 105 of FIG. 2 or of the sampling tubules 68 of FIG. 3. A suspension of the captured particles is then carried over into the expansion chamber 7 [FIGS. 1, 2, and 4] and thence through the liquid-retaining channel 54 [FIG. 4] to line 21, valving 17, and line 23 into the concentrator 25, where the particles are transferred into a tiny volume of aqueous solution that is ready for testing in detector 25, in accordance with the above-explained scheme of FIG. 5.

3. Monitoring for Insect-Borne Pathogens

A recent article by J. Morris, "When a pest turns menace," U.S. News & World Report, Apr. 3, 2000, pp. 48–49, discusses the menace posed by mosquitoes in transmitting deadly pathogens, such as "dengue, malaria, yellow fever, and various forms of encephalitis, including West Nile." Now, the suction at the air intake of a PHTLAAS is strong enough to draw in any nearby mosquitoes, and the trapped mosquitoes could be tested for the above-cited pathogens.

The high air velocity at the air intake and the rapid swirling motion of the air within the PHTLAAS is strong enough to hurl any caught mosquitoes against the inner wall of the sampling tube 105 or 68. If a non-aqueous liquid, such as mineral oil is used as the carrier, then any mosquito not killed by impacting the wall will be drowned or choked by the oil film on that wall. If an aqueous solution is used as the carrier, then inclusion of any insecticide, such as Malathion, will assure the death of any impacting mosquito. If the insecticide is a cell lysing agent, such as tris [hydroxymethyl]aminomethane or the commercial product microLYSIS, supplied by Microzone Limited, Lewes, East Sussex, United Kingdom, then a sufficient quantity of DNA from a deadly virus or other pathogen may get dissolved or suspended in the carrier liquid to be amenable to identification by PCR [Polymerase Chain Reaction] or immunoassay techniques.

To increase the effectiveness of a PHTLAAS in capturing a sufficient number of mosquitoes for conclusive identification of pathogen threats, use can be made of known mosquito attractants, such as lighting, heat, and such chemical attractants as carbon dioxide from controlled sublimation of dry ice or controlled combustion of a flammable organic substance [propane, alcohol, or the like], lactic acid and/or 1-octen-3-ol. The chemical attractants may be either fed into the carrier liquid from one of the reservoirs 13, 13' . . . and transferred at a controlled rate into the sampled air stream or else they can be injected through a separate line [not shown] into the exhaust air that is emanating from the PHTLAAS. To distribute such attractants over a wide area, the exhaust air should be emitted from a large opening through a wide angle.

The following potential advantages are seen in using HTLAAS devices rather than other known mosquito traps. First, the suction at the air intake and the high air sampling rate of some 300 L/min or faster assure that a much larger number of approaching mosquitoes will be captured than with passive insect traps. Furthermore, the concentration of chemical attractants in the exhausted air can be controlled far better than with other devices using the system of FIG. 1, and that concentration can be optimized to attract mosquitoes and other blood-sucking insects from a much wider area. Moreover, the composition of the carrier liquid can be controlled so as to not only assure instant death or incapacitation of any impacting insects but also to facilitate lysis of the insects' cells and transfer of the suspended insects, their lysed cells, and their released DNA components for appropriate testing and pathogen identification procedures.

4. Monitoring for Lead, Hexavalent Chromium, and Other Hazardous Metals and Their Compounds Besides monitoring for solely airborne hazards, a HTLAAS instrument can be provided with a dual-line air exhaust and air intake adapter and used to detect lead, hexavalent chromium, and other hazardous metals and their compounds in crumbling walls or paint, in soils, especially sand, and in other contaminated areas. The ability of the PHTLAAS to collect both vapors and aerosols from the sampled air should be especially useful in applications where a significant fraction of the airborne analyte may be in form of vapor (e.g., organometallic compounds, such as methyl mercury or tetraethyl lead), solid particles or liquid droplets.

The extractant that is to be used in preferred embodiments of the invention will depend on the analyte of interest. To dissolve lead compounds, such as lead oxide (PbO), lead carbonate ($PbCO_3$), or lead nitrate ($Pb(NO_3)_2$), a solution of acetic acid or acetate may suffice, as disclosed in detail in my afore-cited co-pending applications Ser. Nos. 08/377,966 and 08/851,428. To solubilize metallic lead, an oxidant needs to be added to the extractant. The effect of pH and of acetic acid, acetate, and oxidant concentrations in water on the rate of solubilization of metallic lead at 20° C. is shown in FIGS. 4–6 of the co-pending application Ser. No. 08/377,966. At a pH of 5 or less, as little as 0.1 M of sodium acetate or acetic acid plus 1 weight-% $H_2O_2$ suffices to yield an etching rate of about 10 microns/min, which implies that particulates in the respirable size range of <5 microns will completely dissolve in such a solution within a fraction of a minute.

Indeed, when 1-mL portions of an extractant containing 0.3 M acetic acid plus 3% hydrogen peroxide were added to 1-mg samples of powdered lead carbonate (passed through a 325×325 mesh gauze that retained particles of sizes >40 microns), lead oxide, or lead nitrate, complete dissolution of the powders occurred within less than a minute. It therefore appears that a solution containing 0.1–1 M of acetic acid or acetate ions plus 1–10% of hydrogen peroxide is adequate for the solubilization of lead-containing particulates, provided that its acidity is kept at a pH of 5 or less. Furthermore, for use with the PHTLAAS, the preferred concentration range is 0.1–0.3 M of acetic acid plus acetate ions and 1–3% of hydrogen peroxide.

The analytical means that is to be used will again depend on the analyte of interest. For the detection of lead in aqueous solutions under field conditions, a colorimetric or electroanalytical method appears to be more cost effective than an alternative method based on atomic absorption spectroscopy (NIOSH Method 7082), especially for use under field conditions, as detailed in my above-cited co-pending applications.

Similarly, to screen for $Cr^{+6}$ compounds, the concentration of carcinogenic $Cr^{+6}$ can be measured by a technique which uses an aqueous alkaline solution, as described in publications by S. A. Katz, "The Analytical Biochemistry of Chromium," Environ. Health Perspect., 92:13–16 (1991), and D. C. Greene, S. Pepe, F. Dolinsek, and S. A. Katz, "Determination of Hexavalent Chromium in Some Contaminated Soils from Hudson County, New Jersey," J. Environ. Sci. Health, A27(3):577–586(1992). Samples collected by the PHTLAAS should be readily analyzable by this technique.

Portable kits for the determination of $Cr^{+6}$ in water are marketed by the Hach Co. [Loveland, Colo. 80539]. Their listed "smallest increment" of 0.05–0.1 mg/l translates to a detection limit for $Cr^{+6}$ of about 0.01 $mg/m^3$ of air using a PHTLAAS that samples air at a rate of 200–300 l/min for 3–5 minutes and collects the contaminants into a liquid volume of about 10 ml at an efficiency of 20–30%.

If it is desired to monitor solely the content of respirable particulates, a flow-deflecting large-particle impactor, such as that shown in FIG. 2, may be interposed at the air intake so as to collect the larger particles outside the PHTLAAS, while allowing the smaller particles to flow unhindered through the intake with the sampled air.

5. Testing Soils, Homes, Work Areas, and Ambient Air for Potential Carcinogens

In attempts to reduce people's exposure to cancer-inducing soil and air contaminants, the conventional, rather laborious and expensive procedure is to test soils and air for the presence of specific known or potential carcinogens frequently using costly instrumentation and analytical methods that were developed and preferably approved by the Environmental Protection Agency for each specific substance. This approach may be appropriate in cases where only a few carcinogens are expected to pose a potential hazard to be monitored. For instance, in many industries, laboratories, offices, and even homes, formaldehyde may pose a fairly widespread cancer hazard which can be detected with PHTLAAS instruments [see C. S. Woo, S. E. Barry, and S. Zaromb, "Detection and Estimation of Part-per-Billion Levels of Formaldehyde Using a Portable High-Throughput Liquid Absorption Air Sampler." *Environ. Sci. Technol.* 32:169–176 (1998)]. In decommissioned or malfunctioning nuclear reactors, tritiated water may pose a radio-activity threat which may be monitored as described in a paper by S. Zaromb, A. Justus, W. Munyon, D. Reilly, and B. Chen, "A Novel Portable Grab Sampler for Tritiated Water Vapor." *Health Phys.* 72(3):480–484 (1997)]. However, this approach has turns out to be costly and ineffective where more than a few potential carcinogens may be present or where the hazard is posed by an unknown carcinogen. For instance, the cause of a mysterious incidence of brain tumors among employees of an Amoco laboratory in Illinois has never been discovered, in spite of all the elaborate and expensive tests that were conducted in futile attempts to pinpoint it.

A far more effective and far less expensive alert to a probable presence of carcinogens in ambient air, or in contaminated soils, homes or work areas, is based on a combination of a HTLAAS technology with any one of the established tests for mutagenicity of aqueous samples, such as the well known, relatively inexpensive but slow Ames test or the more costly but faster Mutatox tests, as discussed below. These tests have so far been used solely for water-containing samples. By subjecting the pollutant-enriched water samples that are collected by a HTLAAS to either of these mutagenicity tests, we provide an effective and relatively inexpensive alert for soil-impregnated or airborne carcinogens and other mutagens. Also, with a dual-line intake-exhaust adapter, as per the scheme of FIG. 1, it is also possible to use the same approach to contaminant-impregnated soils, work areas, or even homes.

Relatively inexpensive "Mutagen Detection Ames Modules" are available from Microbix Education Systems, Toronto, Canada. Although an Ames test takes several days to complete, each module permits simultaneou testing of many samples for carcinogens and other mutagens, so that the average time per test is effectively short.

Much faster but much more expensive testing can be performed with a Microtox/Mutatox System, supplied by AZUR Environmental, Carlsbad, Calif., which can test aqueous samples for acute toxicity, chronic toxicity, and mutagenicity. Contaminant-enriched water samples from a HTLAAS device could be tested not only for mutagenicity but also for acute or chronic toxicity using a technology that is based on the respiratory physiology of Vibrio fischeri (formerly, Photobacterium phosphoreum), a naturally luminescent marine bacterium. When properly maintained and grown, certain strains of luminescent bacteria divert about ten percent of their metabolic energy into a special metabolic pathway that converts chemical energy, through the electron transport system, into visible light. This pathway is intrinsically linked to the respiration of the cell [A. A. Bulich, 1979. "Use of luminescent bacteria for determining toxicity in aquatic environments." In: *Aquatic Toxicology*, ASTM STP 667, L. L. Marking and R. A. Kimerle, Eds., American Society for Testing and Materials, pp. 98–106].

The test for acute toxicity measures a decrease in light output. A change in cellular metabolism or a disruption of the cellular structure results in a change in respiration and a concomitant change in bioluminescence. This physiological endpoint is used to monitor the "health" of the cells before and after a fifteen-minute exposure [P. E. Ross, 1993. "The Use of Bacterial Luminescence Systems in Aquatic Toxicity Testing." Chapter 13 in: M. Richardson (ed.) *Ecotoxicology Monitoring*. VCH Publishers, New York]. Toxicity is estimated as a function of inhibition of luminescence, relative to controls, in a concentration-response relationship. The test for chronic toxicity uses the same measurement (inhibition of luminescence) but at a sensitivity that is heightened with a longer exposure time, so that lower concentrations of toxicants can be detected [see the above-cited Ross, 1993].

The test for genotoxicity, or mutagenicity, uses a mutant strain of V. fischeri in which the luminescence capability is repressed [S. Ulitzur, I. Weiser and S. Yannai. 1980. "A new sensitive and simple bioluminescence test for mutagenic compounds." *Mut. Res.* 74: 133–124]. When this dark mutant strain is exposed to genotoxic chemicals, some of the cells will undergo the reverse mutation, becoming luminescent [K. K. Kwan, B. J. Dutka, S. S. Rao and D. Liu. 1990. "Mutatox test: a new test for monitoring environmental genotoxic agents." *Environmental Pollution*. 65: 323–332]. Three types of mutagens have been detected with the Mutatox test: direct mutagens (base-substitution or frame-shift agents); DNA damaging agents or DNA synthesis inhibitors; and, DNA-intercalating agents [S. Ulitzur, 1986. "Bioluminescence test for genotoxic agents." *Methods in Enzymology*. 133: 264–274]. Genotoxic potential is estimated as a function of increase in luminescence, relative to controls.

The Mutatox assay for genotoxic agents uses the dark mutant strain of V. fischeri in which a forward mutation has disabled the luminescence capability of the cell. The test system is comprised of freeze-dried luminescent bacteria of the dark mutant strain, a temperature-controlled photometer, and a data capture and analysis protocol supplied via a desk-top computer. Standardization is maintained by supplying cells in a freeze-dried form designed to capture and maintain their optimum physiological state. This method of preservation assures consistent sensitivity and specificity of the test. A range of sample concentrations is tested, and a luminescence response greater than three times the control luminescence is considered to be a genotoxic event.

There will now be obvious many variations and modifications of the afore-disclosed embodiments to persons skilled in the art. It will be obvious that similar approaches can apply to the detection and monitoring of illicit drugs and many hazardous substances, e.g., comprising cadmium, zinc, chromium, uranium, or compounds of these metals, miscellaneous carcinogens, and other toxic contaminants, that can be either absorbed directly in a suitable liquid extractant or solubilized therein from collected airborne particulates. All of these variations and modifications will remain within the scope of this invention if defined by the following claims.

What is claimed is:

1. Apparatus for detecting the presence of a harmful substance or trace thereof comprising:

means for collecting said substance or trace from a volume of air into a volume of a liquid carrier; and means for transferring said carrier into an appropriate detector, wherein said collecting means comprises:

a container with an air inlet opening and an air exhaust opening;

an air pumping means for moving air through said openings;

means for extracting said substance or trace from collected particulates or insects into a volume of carrier liquid so as to form an analyte-enriched liquid sample; and an air intake line extending from said inlet opening and leading to an intake aperture for drawing air into said inlet opening from selected spaces.

2. The apparatus of claim 1, comprising an outlet line with an outlet aperture for blowing exhaust air from said outlet aperture onto selected surface so as to blow off insects, particulates or liquid droplets therefrom, wherein said apertures are held together by a fixture and their relative positions and orientations are so adjusted that many of the blown off insects, particulates or droplets are drawn through said intake line into said collecting means.

3. The apparatus of claim 1, wherein said detector appertains to the family of devices utilizing immunosensor or polymerase chain reaction technology.

4. Apparatus for detecting the presence of a harmful substance or trace thereof comprising:

means for collecting said substance or trace from a volume of air into a volume of a liquid carrier; and means for transferring said carrier into an appropriate detector, wherein said collecting means comprises:

a container with an air inlet opening and an air exhaust opening;

an air pumping means for moving air through said openings;

means for extracting said substance or trace from collected particulates or insects into a volume of carrier liquid so as to form an analyte-enriched liquid sample; and a flow expansion chamber leading to an exhaust fan rotor and a baffle ahead of and co-rotating with said rotor for minimizing entrainment of particles or droplets with the air that is exhausted through said fan.

5. The apparatus of claim 4 comprising a liquid input chamber below said air inlet opening and means for either recirculating liquid from said expansion chamber back into said input chamber or for transferring said liquid to said detector, wherein said recirculating or transferring means comprises an electrically controllable valve.

6. The apparatus of claim 5, wherein said container comprises at least three substantially similar parallel sampling tubules through which said moving air must pass on its way to said expansion chamber in a swirling and highly turbulent motion.

7. The apparatus of claim 5, wherein said extracting means comprises liquid reservoirs, liquid pumping means, connecting tubing, and electrically controlled valving means for feeding one or more liquid extractants to said input chamber, wherein said liquid pumping and valving means is electrically programmable to permit introduction of an appropriate extractant into said input chamber in predetermined quantities at predetermined times.

8. The apparatus of claim 7 comprising a solenoid air flow control valve and electrically programmable air pumping and valve control means for adjusting the rates of air flow through said container in accordance with a predetermined timing cycle.

9. Apparatus for detecting the presence of a harmful substance or trace thereof comprising:

means for collecting said substance or trace from a volume of air into a volume of a liquid carrier; and means for transferring said carrier into an appropriate detector, wherein said collecting means comprises:

a container with an air inlet opening and an air exhaust opening, an air pumping means for moving air through said openings; and means for extracting said substance or trace from collected particulates or insects into a volume of carrier liquid so as to form an analyte-enriched liquid sample, wherein said liquid carrier has a lower density and a substantially lower freezing point and much lower vapor pressure than water, so that it will function satisfactorily in both cold sub-freezing and hot equatorial weather without being affected by humidity conditions.

10. The apparatus of claim 9 comprising means of transferring suspended particulates, including microorganisms or small insects, from said low-density liquid to a volume of an aqueous medium by causing droplets of said medium to sink through said liquid.

* * * * *